United States Patent [19]
Eden et al.

[11] Patent Number: 4,740,642
[45] Date of Patent: Apr. 26, 1988

[54] CATALYST AND PROCESS FOR THE FLUID-BED OXYCHLORINATION OF ETHYLENE TO EDC

[75] Inventors: Jamal S. Eden, Akron; Joseph A. Cowfer, Medina, both of Ohio

[73] Assignee: The BF Goodrich Company, Akron, Ohio

[21] Appl. No.: 898,566

[22] Filed: Aug. 21, 1986

[51] Int. Cl.⁴ .................. C07C 17/156; C07C 17/02
[52] U.S. Cl. ..................................... 570/243; 502/225
[58] Field of Search ......................................... 570/243

[56] References Cited

U.S. PATENT DOCUMENTS

3,210,431 10/1965 Engel .................................. 570/243
3,816,554 6/1974 Reni et al. ........................... 570/243

*Primary Examiner*—J. E. Evans
*Attorney, Agent, or Firm*—Alan A. Csontos

[57] ABSTRACT

A fluidizable catalyst composition is provided containing about 2% to about 8% by weight of copper (about 4% to about 17% by weight of copper salt), from about 0.2% to about 10% by weight of a rare earth metal salt(s), preferably the chloride salt(s), and from about 0.25% to about 2.3% by weight of an alkali metal salt(s), preferably the chloride salt(s), all weight percents based upon the total weight of the catalyst composition. The metals are codeposited on a fluidizable, high surface area alumina support. The weight of the alkali metal employed is not over 2.5% by weight (as the chloride) and the weight ratio of the rare earth metal salt(s) to the alkali metal salt(s) must be at least 0.8:1. Such catalyst compositions are extremely useful as fluid bed catalysts in the vapor phase oxychlorination reaction of ethylene, oxygen and hydrogen chloride to produce 1,2-dichloroethane (EDC). The use of the catalysts results in improved, high percent ethylene efficiencies and high percent HCl conversions, and avoids operating problems caused by stickiness of the catalyst in the fluid bed. A combination of copper chloride, potassium chloride and one or more of the rare earth chlorides on a fluidizable gamma alumina support, produces an excellent catalyst for a fluid bed ethylene oxychlorination process.

6 Claims, 1 Drawing Sheet

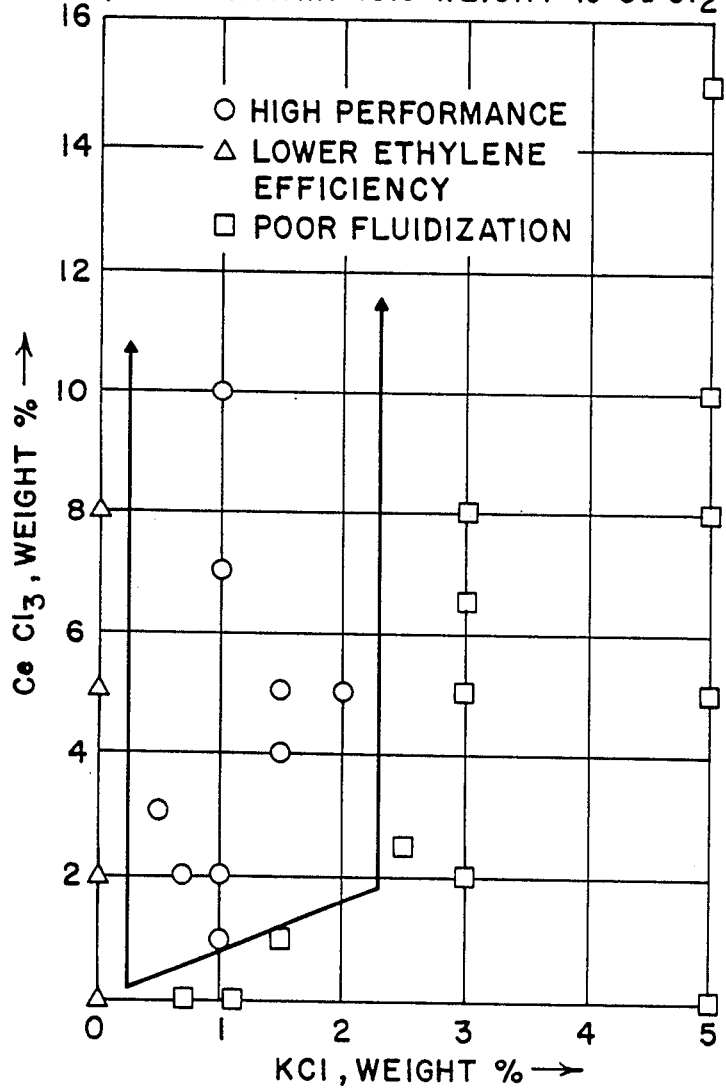

CATALYST AND PROCESS FOR THE FLUID-BED OXYCHLORINATION OF ETHYLENE TO EDC

BACKGROUND OF THE INVENTION AND REFERENCES TO THE PRIOR ART

This invention pertains to fluid bed, catalytic oxychlorination of ethylene to produce 1,2 dichloroethane, commonly called ethylene dichloride (EDC), and relates specifically to improved copper chloride catalysts and their use in an ethylene oxychlorination reaction.

The production of chlorinated hydrocarbons by oxychlorination is known to the art. For example, a well known process for oxychlorination of ethylene to produce EDC, practiced in many commercial installations throughout the world, involves the vapor phase reaction, over a fluidized catalyst bed, of a mixture of ethylene, hydrogen chloride (HCl) and oxygen or an oxygen containing gas (e.g., air) in the manner and under the conditions described in U.S. Pat. No. 3,488,398 granted to Harpring et al.

A typical catalyst used in fluid bed oxychlorination reactions comprises about 4% to 17% by weight of a copper compound. Typically, the copper compound is cupric chloride, as the active catalytic ingredient, deposited on particles of a fluidizable support, such as silica, kieselguhr, clay, fuller's earth, or alumina. The support should be readily fluidizable without excessive catalyst loss from the reaction zone, and have proper bulk density, resistance to attrition and particle size and distribution to be useful in the process. In prior art oxychlorination processess most closely aligned to the present invention, an alumina support is employed which may be gamma alumina, alpha alumina, the so-called microgel aluminas or other forms of "activated" alumina. The standard, fluid bed alumina-based oxychlorination catalysts can be improved upon in significant respects.

First, it is desirable for the oxychlorination catalyst to effect the highest possible yield of EDC based on ethylene (i.e., for the ethylene to be more completely converted to EDC, with less ethylene being reacted to carbon oxides or higher chlorinated materials). In the high volume business of manufacturing EDC, small increases in the efficiency of ethylene conversion to EDC are very valuable. For example, in a one billion pound per year EDC oxychlorination plant, an ethylene efficiency increase of only 1% can result in a savings of from about 0.4 to about 1.0 million dollars annually. Further, increased ethylene efficiency reduces the potential of release of hydrocarbons and chlorinated hydrocarbons to the environment.

Second, it is becoming much more desirable for economic and environmental reasons, for the oxychlorination catalyst to also effect a high conversion of the hydrogen chloride (HCl) used in the reaction. Problems can arise when a higher than theoretical molar ratio of HCl to ethylene is used in an attempt to achieve higher ethylene conversions to EDC. Unconverted HCl must be neutralized using, for example, a caustic solution, and the resulting salt must be disposed. Also, higher levels of HCl in the process can lead to higher HCl "break through" downstream of the reactor which can cause corrosion problems. Hence, a modern oxychlorination process will attempt to operate at an HCl to ethylene molar ratio as close to the theoretical level of two-to-one (2:1) as possible in conjunction with high HCl conversion. In such an operation, a combination of high HCL conversion and high ethylene efficiency is most desirable.

Lastly, typical cupric chloride on alumina, fluid bed catalysts exhibit a strong tendency to develop "stickiness" during the oxychlorination reaction at HCl to ethylene molar feed ratios of about 1.9 to 2.0. Catalyst stickiness, which is basically agglomeration of catalyst particles, is a critical barrier to achieving optimum ethylene and HCl feedstock efficiencies in a fluid bed oxychlorination process. High ethylene efficiency from an oxychlorination catalyst requires operation with an HCl/ethylene molar feed ratio approaching the stoichiometric value of 2.0. However, as the HCl/ethylene feed ratio is increased above about 1.9 in a commercial process, standard fluid bed oxychlorination catalysts become progressively more sticky. With increased catalyst stickiness, heat transfer characteristics of the fluid bed worsen, hot spots develop within the catalyst bed, feedstock conversions and yields decline, and, in extreme cases, the bed actually collapses and slumps causing vapor passages through the bed. Therefore, a high performance oxychlorination catalyst requires operation with HCl/ethylene feed ratios approaching 2.0, excellent fluidization, and high conversions, yields, and efficiencies. This problem of catalyst stickiness and a device and means for its partial control are described in U.S. Pat. No. 4,226,798 issued to Cowfer et al. A method of controlling stickiness in standard oxychlorination catalysts is also described in U.S. Pat. No. 4,339,620 also issued to Cowfer et al. Although these devices and methods are helpful, it is more practial and efficient to employ an oxychlorination catalyst which does not develop stickiness during the reaction.

By way of further background, it has been proposed in the prior art to conduct oxychlorination reactions using a fluid bed catalyst in which the catalyst contains not only copper chloride but other metal compounds such as chlorides and oxides of alkali metals, alkaline earth metals, transition metals, and/or rare earth metals. For example, U.S. Pat. No. 3,427,359 describes a catalyst composition useful for fluid-bed oxychlorination of hydrocarbons consisting of copper chloride, an alkali metal chloride and/or a rare earth metal chloride supported on an alpha alumina having a surface area no greater than 10 $m^2/g$. Likewise, U.S. Pat. Nos. 3,657,367; 3,914,328; 3,992,463; 4,069,170; 4,124,534 and 4,284,833 and Canadian Pat. No. 701,913 all teach the use of metal chlorides deposited with copper chloride on low surface area (alumina) supports. However, these low surface area support catalysts are not useful in the fluid bed ethylene oxychlorination process of the present invention because the ethylene efficiency is very low.

There are also patents which disclose the use of alkali metals, alkaline earth metals, and/or rare earth metals along with copper chloride on high surface area supports. For example, U.S. Pat. Nos. 3,468,968; 3,642,921; and 4,123,389 all broadly disclose the use of a catalyst of copper chloride and alkali metals such as KCl, and/or rare earth metals such as cerium, praeseodymium, neodymium, and lanthamum. Whereas these catalysts are closer in composition to those of the present invention, optimization in composition and improvements in performance can still be obtained. All of these references are deficient in that none teach or suggest the optimization of the ratio of the types of metals used to each other in affecting catalyst performance.

Lastly, other patents in the prior art do teach or suggest that better catalysts are obtained if the added metals are employed in a certain weight or molar ratio of added metal(s) to the copper present. For example, U.S. Pat. Nos. 3,205,280; 3,308,189; 3,308,197; 3,527,819; 3,769,362; 3,862,996; 4,046,821; 4,123,467; 4,206,180; 4,239,527; 4,329,527; 4,451,683 and 4,460,699 all broadly disclose that a certain weight or mole ratio of added metal to copper improves the catalyst.

From the above, it is readily seen that much effort has been put into developing "optimum" catalysts for oxychlorination reactions. Of all the above-referenced patents, it is worthwhile to note those patents most closely aligned with the catalyst and process of the present invention. U.S. Pat. No. 3,205,280 discloses a catalyst composition of an $Al_2O_3$ support (calcined at 900° C. which substantially lowers its surface area) having thereon an alkali metal such as potassium chloride, an alkaline earth metal, a transition metal such as copper, and/or a rare earth metal such as didymium. The atomic ratio of alkali or alkaline earth metal to transition or rare earth metal is at least one-to-one to no more than seven-to-one. Preferably, the patent teaches an atomic ratio of alkali metal to transition metal to rare earth metal of 4:1:1. A catalyst of KCl, $DiCl_2$, and $CuCl_2$ on alpha-$Al_2O_3$ is shown in Example IV.

U.S. Pat. No. 3,308,197 broadly teaches a catalyst composition of aluminum oxide containing Group Ia and/or IIa metals such as potassium chloride and a Group IIIb metal such as ceric oxide, wherein the ratio of metal atoms from Groups Ia and IIa to Group IIIb is from 0.01 to 1.5:1. A catalyst of $CeO_2$ and KOH on Vycor Raschig rings is disclosed in Example 6.

U.S. Pat. No. 3,527,819 broadly teaches a process for preparing tri-and tetrachloroethylene using a catalyst composition of copper chloride, potassium chloride, and neodymium chloride on a high surface area silica gel support. The atomic ratio of potassium to copper in the catalyst is 0.6 to 1:3 to 1, and the atomic ratio of neodymium to copper is at least 0.4 to 1. The patent's teaching is specific to neodymium chloride. However, comparative catalysts containing up to 2.5% by weight of rare earth metals are shown in Table 1.

U.S. Pat. No. 3,862,996 broadly teaches a process for preparing ethylene from ethane using a catalyst composition of an alumina support containing copper halide and a rare earth metal halide, and optionally an alkali metal halide such as KCl or LiCl. The weight ratio of rare earth metal halide to copper halide in the catalyst is greater than one-to-one. A catalyst of $CuCl_2$, rare earth metal halide (cerium halide and didymium halide) and LiCl on an alumina support is shown in the Examples.

U.S. Pat. No. 4,046,821 broadly teaches a catalyst composition of a low surface area support containing a copper (non-halide) compound such as $CuCO_3$, a rare earth metal compound, and optionally an alkali metal compouond. The atomic ratio of rare earth metal to copper in the catalyst is 4 to 0.1 to 1. Catalysts of $CuCO_3$, $CeO_2$ and KCl on a low surface area alumina are shown.

Lastly, U.S. Pat. No. 4,451,683 broadly teaches a catalyst composition of a copper compound such as $CuCl_2$, an alkali metal such as KCl, and a rare earth metal such as $CeCl_3$ on a high surface area magnesium oxide—aluminum oxide support. The number of alkali metal ions in the catalyst is less than 100 per 100 ions of copper. A catalyst of $CuCl_2$, KCl, and $CeCl_3$ on a high surface area MgO, $Al_2O_3$, $Na_2O$ support is shown in Table 3.

The deficiency in the above patents is that none of these patents teach or disclose the effect of the ratio of rare earth metal to alkali metal on catalyst stickiness and performance.

As a final prior art reference, U.S. Pat. No. 4,446,249, issued to J. Eden, one of the present inventors, discloses a method of obtaining an improved oxychlorination catalyst of cupric chloride on a gamma-alumina support, modified with one or more of an alkali metal, an alkaline earth metal, and/or a rare earth metal wherein the critical feature of the patent consists of "fixing" the modifying metal(s) to the support by a calcination step prior to deposition of the cupric chloride. The pre-calcination of the modifying metal(s) to the support before adding the copper makes the catalyst composition less prone to stickiness during use. The catalysts of the present invention are distinguished over this prior art in that, in the present invention, a fluidizable (non-sticky), high ethylene efficiency, high HCl conversion catalyst is obtained without the need of calcining the alkali metal and rare earth metal to the support before depositing the cupric chloride.

SUMMARY OF THE INVENTION

The catalyst compositions of the invention are highly fluidizable catalysts of a high surface area alumina support having thereon copper chloride, at least one alkali metal and at least one rare earth metal. The catalysts compositions are prepared by co-depositing the metals on the high surface area alumina support without the need of first calcining the non-copper metals to the support, provided that the weight ratio of rare earth metal salt(s) to alkali metal salt(s) is at least 0.8:1. The use of the catalyst compositions of the invention in the oxychlorination of ethylene to EDC results in high percent ethylene efficiency and percent HCl conversion without exhibiting catalyst stickiness.

BRIEF DESCRIPTION OF THE DRAWING

The FIGURE depicts the performance of various catalyst compositions in an oxychlorination reaction in terms of high performance, which is a combination of high ethylene efficiency, high HCl conversion, and good fluidization. All the catalysts shown in the drawing contained 10.6% by weight of the copper compound (cupric chloride) in addition to the indicated weight percents of the alkali metal salt (potassium chloride) and rare earth metal salt (cerium chloride). All oxychlorination reactions were conducted at a molar ratio of ethylene to HCl to oxygen of 1:2:0.8, at a temperature of 225°±1° C., and a contact time (defined for a settled bed) of 22±0.5 seconds.

The abscissa is weight percent of alkali metal salt (potassium chloride) contained on the catalyst composition. The ordinant is weight percent of rare earth metal salt (cerium chloride) contained on the catalyst composition. The envelope imposed on the graph represents the area of high performance in which both high ethylene efficiency and high HCl conversion along with good catalyst fluidization is obtained. The catalyst compositions of the invention fall into the high performance area. Poor fluidization occurs when too high of a level of alkali metal salt is used or the weight ratio of rare earth metal salt to alkali metal salt is too low.

DETAILED DESCRIPTION OF THE INVENTION

The catalyst compositions of this invention employ high surface alumina support materials which are readily available. The alumina support material has a surface area in the range of about 80 to 200 m$^2$/g, a compacted bulk density in the range of 0.9 to 1.1 grams per c.c., a pore volume in the range of 0.2 to 0.5 c.c. per gram and a particle size distribution such that about 70 to 95 weight percent of the particles are below 80 microns in diameter, about 30 to 50 percent are below 45 microns in diameter, and about 15 to 30 percent are below 30 microns in diameter, with no more than 5% of the particles larger than 200 microns or more and no more than 10% of the particles smaller than 20 microns. Such alumina support materials are readily fluidizable, relatively stable, mechanically strong and resistant to attrition. Alumina supports that meet the above criteria are sold by Harshaw/Filtrol Partnership, Ketjen Catalysts, and other catalyst suppliers.

It is recognized that some alumina support materials may contain in addition to aluminum oxide ($Al_2O_3$) traces of other metals such as metal oxides like sodium oxide. These alumina supports are readily useable in this invention.

The alkali metal employed in the present invention can be sodium, potassium, lithium, rubidium, or cesium, or a mixture of one or more such metals. The alkali metal is used in the form of a water soluble salt, and preferably is used in the form of an alkali metal chloride. However, other alkali metal salts that would convert to the chloride salt during the oxychlorination process can also be used, such as the carbonate salt or other halide salts like the bromide salts. The alkali metal is used in the range from about 0.25% to about 2.3% by weight (as the chloride) based on the total weight of the catalyst composition. The preferred alkali metals are potassium, lithium, and cesium. The most preferred alkali metal is potassium, and the preferred alkali metal salt is potassium chloride used at from about 0.5% to 2% by weight based on the total weight of the catalyst.

The rare earth metal employed in the invention can be any of the elements listed as elements 57 through 71 of the Periodic Table. Examples of rare earth metals include lanthanum, cerium, praeseodymium, neodymium, or naturally occurring mixtures of one or more such metals such as didymium. The rare earth metal is used in the form of a water soluble salt, and preferably is used in the form of a rare earth metal chloride. However, other rare earth metal salts which would convert to the chloride during the oxychlorination process can also be used, such as the carbonate salt or other halide salts like the bromide salt. The rare earth metal is used in the range from about 0.2% to about 15% by weight (as the chloride) based on the total weight of the catalyst composition. The preferred rare earth metals are cerium, lanthanum, praeseodymium, and neodymium. The most preferred rare earth metal is cerium, and the preferred rare earth metal salt is cerium chloride used at from about 1% to 10% by weight.

Addition of the metals onto the alumina support is accomplished by impregnating the support with an aqueous solution of a water soluble salt of the metals along with a water soluble salt of the copper compound and then drying the wetted support. The alkali metal and rare earth metal salts do not have to be calcined on the support prior to deposition of the copper compound to produce a fluidizable catalyst, as long as the weight ratio of rare earth metal salt(s) to alkali metal salt(s) is at least (as the chloride) 0.8:1 and the total amount of alkali metal salt(s) in the alumina support is under 2.5% by weight. More preferredly, the weight ratio of rare earth metal salt(s) to alkali metal salt(s) is from one-to-one (1:1) to about thirty-to-one (30:1), and even more preferably from about two-to-one (2:1) to about ten-to-one (10:1).

It was surprisingly discovered that only a particular range of loadings of copper, alkali metals, and rare earth metals and only particular ratios of rare earth metals to alkali metals would result in all of the high performance characteristics described above. Outside of the particular loadings and ratios of the active metals, high performance is not achieved either because the catalyst composition becomes sticky and/or lower percent ethylene efficiency and percent HCl conversion is obtained.

The copper compound is also used in the form of a water soluble salt, and preferably is used in the form of cupric chloride. However, other copper salts that would convert to the chloride during the oxychlorination proces can also be used, such as the carbonate salt or other halide salts like the bromide salt. The copper salt is deposited on the alumina support using the same techniques as described above. The amount of copper deposited is based on the activity desired and the specific fluidization characteristics of the support. The amount of copper employed is in the range from about 2% by weight to about 8% by weight as copper metal, from about 4% to about 17% by weight as the copper salt, both based on the total weight of the catalyst composition. More preferredly, the copper salt is employed in the range from about 8% to about 12% by weight, and the most preferred copper salt is copper chloride. The final catalyst composition containing the alkali metal(s), rare earth metal(s) and copper compound is readily fluidiable. However, certain specific characteristics such as surface area and pore volume, for example, are, of course, modified by reason of the deposit of the metals. Hence, the catalyst compositions of this invention have a final surface area in the range of about 70 to about 160 M$^2$/g, which is about 10% to 30% lower than that of the alumina support before the deposit of the metals. The preferred range of surface area for the catalysts is about 85 to about 125 m$^2$/g.

Other metals can be present in the catalyst compositions of the invention in relatively small amounts. For example, alkaline earth metals and/or transition metals can be present in up to about 1% by weight total based on the total weight of the catalyst composition. Examples of such other metals are magnesium, barium, iron, and the like.

The catalyst compositions of this invention are readily prepared by wetting the alumina support material, as above described, with an aqueous solution of a salt(s) of the desired metals. The wetted alumina is then dried at about 80° C. to 110° C. to remove water. An amount of the metal salt is chosen so that the final catalyst contains from about 0.25% to about 2.3% by weight of the incorporated alkali metal (as the chloride) and from about 0.2% to about 15% by weight of the rare earth metal (as the chloride), both based on the total weight of the catalyst composition. The metal salt used in the aqueous solution can be in the form of any water soluble salt such as previously described, like the chloride or carbonate salt of potassium, sodium, lithium, rubidium or cesium, or of lanthanum, cerium, praeseodymium, neodymium, and didymium (which is a mixture of rare earth metals which contains lanthanum and neodymium together with smaller amounts of praesodymium and samarium and even smaller amounts of rare earth metals). The specific combination of potassium chloride with rare earth metals such as lanthamum, praeseodymium, neodymium, and particularly cerium chloride is particularly desirable.

A critical feature of the catalyst compositions of this invention is that, within the weight ranges of alkali metal and rare earth metal stated herein, the weight ratio of rare earth metal salt(s) to alkali metal salt(s) must be at least 0.8:1 or higher or stickiness, hot spots, and caking occur with use of the catalyst. Whereas prior art processes have advised many techniques to reduce stickiness, it was unexpectedly discovered that catalyst stickiness can be prevented by employing a defined weight level of alkali metal(s) and a defined weight ratio of rare earth metal(s) to alkali metal(s).

The catalyst compositions of the invention are highly efficient catalysts for the oxychlorination of ethylene to EDC. The reaction process temperatures vary from about 190° C. to about 250° C., and more preferredly from about 220° C. to 240° C. Reaction pressures vary from atmospheric to about 70 psig. Contact times in the fluid bed vary from about 10 seconds to about 50 seconds, and more preferably are from about 20 to 35 seconds. The ratio of the ethylene, HCl, and oxygen reactants, based on the moles of HCl charged, range from about 1.0 to about 1.1 moles of ethylene and about 0.5 to about 0.9 mole of oxygen per 2.0 moles of HCl. As previously mentioned, modern oxychlorination processes attempt to operate as close as possible to the stoichiometric ratio of 2 moles of HCl to 1 mole of ethylene.

When the novel catalyst compositions are used under commercial production conditions in the oxychlorination of ethylene to EDC to about 230° C. with about a 30 second fluid bed contact time, the conversion of ethylene is 99% or above and the percent ethylene efficiency is above about 96%. This efficiency compares with a normal commercial ethylene efficiency of about 93 up to 95% obtained using conventional, known catalyst compositions. The percent conversion of HCl is also very high using the catalysts of the present invention, exceeding 99% HCl conversion. The catalyst compositions of this invention are significantly less "sticky" when used under commercial oxychlorination reaction conditions. Accordingly, this invention provides, in addition to improved catalyst compositions, an improved fluid-bed ethylene to EDC oxychlorination process. Laboratory scale processes, operating under higher control and more ideal conditions, yield oven better results.

The specific Examples are set forth below to illustrate the unique and unexpected characteristics of the catalyst compositions of this invention, and are not intended to be limiting of the invention. The Examples particularly point out the criticality of (1) using a high surface area alumina support, (2) using a combination of copper chloride, rare earth metal(s) and alkali metal(s), and (3) employing the correct weights of copper chloride and alkali metal salt(s) and correct weight ratio of the rare earth metal salt(s) to alkali metal salt(s). In all of the Examples, the fluid bed oxychlorination reaction is conducted using a bench scale fluid bed reactor of either 2.2 cm. internal diameter and 107 cm. height or 3.0 cm. internal diameter and 50 cm. height charged with 325 cc. or 250 cc., respectively, of the fluid bed catalyst composition as described. The reactor volume, the amount and packing of catalyst charged to the reactor and reactant flow rates all effect the contact time between reactants and catalyst. The contact times were calculated based on a settled bed of catalyst, and were determined by dividing the settled bed volume by the volumetric flow rate of the feed gases at the reaction temperature and pressure. The reactor is equipped with means for delivering gaseous ethylene, oxygen (as air) and HCl through the fluid bed reactor zone, means for controlling the quantities of reactants and reaction conditions, and means for measuring and ascertaining the composition of the effluent gases to determine the percent HCl conversion, percent yield of EDC, and percent ethylene efficiency.

EXAMPLES

A series of experiments were performed to show the unique features of the catalyst compositions of the invention. In the experiments, the reactants ethylene, oxygen and hydrogen chloride, all in the gas phase, were fed to the reactor in a molar ratio of 1.0 mole of ethylene and 0.8 moles of oxygen for each 2.0 moles of hydrogen chloride. Since it was difficult to achieve a flow rate that would result in an exact theoretical level of HCl to ethylene of 2.0 to 1.0, and the percent HCl conversion is somewhat dependent upon the HCl/ethylene ratio, it was necessary to correct the measured percent HCl conversion to adjust for any deviation from a theoretical ratio of 2 to 1. This was done using the following formula:

$$X_2 = \tfrac{1}{2}(X_1 Y_1)$$

where $X_2$ is the corrected precent HCl conversion (corrected to an exact HCl/ethylene molar feed ratio of 2:1)

$X_1$ is the percent HCl conversion determined by analyzing and measuring all components from the exit stream $Y_1$ is the HCl/ethylene molar feed ratio determined by analyzing and measuring all components from the exit stream.

In applying the above equation to correct the percent HCl conversion value, for any specific value of the HCl/ethylene molar feed ratio within the range of 1.96 to 2.04:1, the values of percent ethylene efficiency and crude EDC purity are assumed to remain essentially constant, so that it is predominantly the value of percent HCl conversion which changes with the slight variations in HCl/ethylene molar feed ratio.

The reactions were conducted at temperatures in the range of about 220° C. to about 230° C. by passing the reactants through the fluidized catalyst bed to form EDC. The catalysts used in the experiments each contained about 10% by weight of cupric chloride as the primary catalytic metal. The fluidizable alumina support used was a gamma alumina having a surface area of 150 to 165 square meters per gram ($m^2/g$). All of the metals were deposited on the fluidizable alumina support by thoroughly mixing the alumina support with an aqueous solution of cupric chloride, the alkali metal chloride, and the rare earth metal chloride, followed by drying the wetted mass to fluidity by heating on a steam bath and/or in an oven at temperatures up to about 275° C. for 4 to 8 hours. The fluidizable catalyst composition had a surface area lower than the starting alumina support by a factor of about 10 to 30 percent.

During the experiment being run (the duration of which was sufficient to assure as much stability in the fluid bed as possible, but was otherwise insignificant) the condition of the catalyst fluid bed in terms of stickiness of the particles was observed and rated. The results of these tests in terms of catalyst stickiness are also reported in the following Examples.

COMPARATIVE EXAMPLE A

In a comparative experiment, a catalyst was prepared containing 10.6% by weight cupric chloride, 1% by weight of a rare earth metal (Lanthanum chloride) and 1% by weight of an alkali metal (Potassium chloride) on an alpha-alumina support, which is a low surface area alumina as disclosed in many U.S. patents such as U.S. Pat. Nos. 3,427,359; 4,069,170; and 4,124,534. The metals were codeposited onto the alumina support using the procedure previously described above. This Comparative catalyst basically differs from the catalyst compositions of the present invention in the type of alumina support employed. The Comparative catalyst was used in an oxychlorination process under conditions as described below with the following results. It is apparent from the data that the use of an alpha-alumina support (low surface area support) results in a very low percent ethylene conversion and low percent ethylene efficiency. Hence, the data shows that the present invention is limited to high surface area alumina supports.

TABLE A

Support: alpha alumina having a surface area of 32 m²/g
Metal salts: KCl, LaCl$_2$, CuCl$_2$
Weight Percent of Metals (as chlorides): 1% K, 1% La, 10.6% Cu
Reactant Feed Ratios: C$_2$H$_4$/O$_2$/HCl = 1.0/0.8/2.0

| Temperature (°C.) | Contact Time (Seconds) | Percent Ethylene Conversion | Percent Yield of EDC | Percent Ethylene Efficiency |
|---|---|---|---|---|
| 225 | 20 | 25.8 | 98.9 | 25.5 |

COMPARATIVE EXAMPLE B

A series of experiments were conducted to demonstrate the effect on catalyst performance of the combination of the alkali metal and the rare earth metal versus the use of either type of metal alone. In these experiments, the alkali metal employed was potassium as KCl, and the rare earth metal employed was cerium as CeCl$_3$. The weight of cupric chloride in the catalyst is 10.6% by weight. The molar feed ratio was 1.0 mole of ethylene to 0.8 mole of oxygen to 2.0 moles of HCl. The percent HCl conversion was measured and then corrected to adjust for any HCl feed variation from a theoretical 2:1 ratio over ethylene. The reactor design described in the specification was employed. A standard oxychlorination catalyst consisting of cupric chloride on a gamma alumina support was prepared and employed as a control. The following data was obtained. Catalyst stickiness was also observed and reported.

TABLE B

| Catalyst | Weight % KCl | Weight % CeCl$_3$ | Temperature (°C.) | Contact Time (Sec.) | % Ethylene Conversion | % Ethylene Efficiency | HCl Conversion Actual | HCl Conversion Corrected | % EDC Yield | Fluidization of Catalyst |
|---|---|---|---|---|---|---|---|---|---|---|
| Control | none | none | 225 | 21.0 | 99.9 | 93.8 | 94.7 | 95.4 | 93.9 | Fluid |
| 1 | 0.7 | none | 225 | 21.0 | 99.0 | 97.3 | 98.2 | 97.6 | 98.3 | Hot Spot |
|  |  |  | 230 | 21.0 | 99.5 | 97.2 | 97.9 | 97.7 | 97.7 | Hot Spots |
|  |  |  | 225 | 31.8 | 99.9 | 97.0 | 98.2 | 97.7 | 97.1 | Hot Spots |
|  |  |  | 230 | 31.8 | 100.0 | 96.1 | 97.9 | 97.3 | 96.1 | Hot Spots |
| 2 | 1.1 | none | 225 | 21.7 | 99.1 | 96.8 | 96.4 | 97.2 | 97.7 | Hot Spot |
|  |  |  | 230 | 21.7 | 99.5 | 96.4 | 97.7 | 97.0 | 96.8 | Poor |
|  |  |  | 225 | 32.3 | 99.9 | 96.6 | 96.1 | 97.2 | 96.7 | Poor |
|  |  |  | 230 | 32.3 | 100.0 | 97.3 | 96.2 | 97.7 | 97.3 | Poor |
| 3 | 5.0 | none | 225 | — | — | — | — | — | — | Severe Stickiness |
| 4 | none | 2.0 | 225 | 21.6 | 99.9 | 97.7 | 98.3 | 99.2 | 97.9 | Fluid |
|  |  |  | 230 | 31.6 | 100.0 | 97.5 | 97.1 | 97.4 | 97.5 | Fluid |
|  |  |  | 225 | 32.2 | 100.0 | 96.2 | 97.1 | 96.8 | 96.2 | Fluid |
|  |  |  | 230 | 32.2 | 100.0 | 95.0 | 96.4 | 95.9 | 95.0 | Fluid |
| 5 | none | 8.0 | 225 | 22.0 | 99.2 | 96.7 | 96.7 | 97.3 | 97.5 | Fluid |
|  |  |  | 230 | 22.0 | 100.0 | 95.9 | 97.0 | 96.9 | 95.9 | Fluid |
|  |  |  | 225 | 32.9 | 100.0 | 94.1 | 96.5 | 95.3 | 94.1 | Fluid |
|  |  |  | 230 | 32.9 | 100.0 | 94.5 | 95.4 | 96.3 | 94.5 | Fluid |
| 6 | 0.7 | 2.0 | 225 | 21.7 | 99.6 | 97.6 | 98.6 | 98.0 | 98.0 | Fluid |
|  |  |  | 230 | 21.7 | 99.9 | 96.6 | 97.4 | 97.4 | 96.7 | Fluid |
|  |  |  | 225 | 32.3 | 100.0 | 96.4 | 97.7 | 97.1 | 96.4 | Fluid |
|  |  |  | 230 | 32.3 | 100.0 | 95.5 | 96.6 | 97.7 | 95.5 | Fluid |
| 7 | 1.5 | 4.0 | 225 | 21.6 | 99.2 | 97.5 | 96.3 | 97.8 | 98.3 | Fluid |
|  |  |  | 230 | 21.6 | 99.7 | 97.6 | 96.7 | 98.2 | 98.0 | Fluid |
|  |  |  | 225 | 32.3 | 99.9 | 97.5 | 97.5 · | 98.1 | 97.5 | Fluid |
|  |  |  | 230 | 32.3 | 100.0 | 96.9 | 96.9 | 98.0 | 96.9 | Fluid |

The data shows that the use of a catalyst of cupric chloride and an alkali metal alone (experiments 1 to 3) can yield higher % Ethylene efficiency and higher %HCl conversion than the Control, but at a disadvantage of progressively worse fluidization in the catalyst bed with higher alkali metal content. At a level of 5 percent by weight of alkali metal (potassium chloride), the catalyst was so sticky that the reaction could not be run. Experiments 4 and 5 show that the use of a catalyst of cupric chloride and a rare earth metal alone can increase % Ethylene efficiency and %HCl conversion over that of the Control, without catalyst stickiness problems. However, percent ethylene efficiency and percent HCl conversion significantly decrease with increasing temperature and contact time. At conditions of commercial processes of about 230° C. and about 30 seconds contact time, lower percent ethylene efficiency (about 94% to 95%) and lower percent HCl conversion (about 96% to 97%) are observed. Experiments 6 and 7 show that high % Ethylene efficiency (about 96% to 97%) and high % HCl conversion (about 97% to 98%) are achieved using the catalysts of this invention. These high efficiencies are obtained over a wide range of operating conditions without any fluidization problems.

COMPARATIVE EXAMPLE C

A series of experiments were conducted to demonstrate the effect on catalyst performance of the weight of alkali metal in the catalyst and the weight ratio of rare earth metal to alkali metal in the catalyst. In these experiments, the alkali metal employed was potassium as KCl, and the rare earth metal employed was cerium as CeCl$_3$. The weight of cupric chloride in the catalyst is 10.6% by weight.

of alkali metal of 2.5 percent or more by weight, no matter that the weight ratio of rare earth metal chloride to alkali metal chloride is 0.8 to 1.0 or above, results in catalyst stickiness. Hence, both the weight ratio and an absolute weight level of alkali metal used must be controlled.

Experiments 2, 5, 6, 7, 8, 12, and 15 employ catalyst compositions of the present invention. In all cases, good fluidization of the catalyst bed was obtained and maintained, and high percent ethylene efficiency and high percent HCl conversion was achieved.

TABLE C

| Catalyst | Weight % KCl | Weight % CeCl$_3$ | Weight Ratio of Rare Earth Metal to Alkali Metal | Percent Ethylene Conversion | Percent Ethylene Efficiency | Percent EDC Yield | Percent HCl Conversion Actual | Percent HCl Conversion Corrected | Fluidizaton of Catalyst |
|---|---|---|---|---|---|---|---|---|---|
| Control | none | none | — | 99.9 | 93.8 | 93.9 | 94.7 | 95.4 | Fluid |
| 1 | 1.5 | 1.0 | 0.7 | 99.4 | 97.8 | 98.4 | 97.2 | 98.2 | Slugging |
| 2 | 0.7 | 2.0 | 2.9 | 99.6 | 97.6 | 98.0 | 98.6 | 98.0 | Fluid |
| 3 | 3.0 | 2.0 | 0.7 | — | — | — | — | — | Severe slugging |
| 4 | 2.5 | 2.5 | 1.0 | — | — | — | — | — | Slugging & caking |
| 5 | 0.5 | 3.0 | 6.0 | 99.6 | 97.8 | 98.2 | 97.3 | 98.1 | Fluid |
| 6 | 1.5 | 4.0 | 2.7 | 99.2 | 97.5 | 98.3 | 96.3 | 97.8 | Fluid |
| 7 | 1.5 | 5.0 | 3.3 | 99.5 | 98.2 | 98.7 | 97.0 | 98.6 | Fluid |
| 8 | 2.0 | 5.0 | 2.5 | 99.7 | 97.9 | 98.2 | 97.6 | 98.6 | Fluid |
| 9 | 3.0 | 5.0 | 1.7 | 99.5 | 97.5 | 98.0 | 95.7 | 98.1 | Severe Slugging |
| 10 | 5.0 | 5.0 | 1.0 | — | — | — | — | — | Caking |
| 11 | 3.0 | 6.5 | 2.2 | — | — | — | — | — | Hot spots & caking |
| 12 | 1.0 | 7.0 | 7.0 | 99.8 | 98.1 | 98.4 | 98.3 | 98.6 | Fluid |
| 13 | 3.0 | 8.0 | 2.7 | — | — | — | — | — | Severe slugging & hot spots |
| 14 | 5.0 | 8.0 | 1.6 | — | — | — | — | — | Severe slugging |
| 15 | 1.0 | 10.0 | 10.0 | 99.0 | 97.7 | 98.7 | 97.5 | 98.0 | Fluid |
| 16 | 5.0 | 10.0 | 2.0 | 97.2 | 96.6 | 99.4 | 96.5 | 96.9 | Severe slugging |
| 17 | 5.0 | 15.0 | 3.0 | 98.7 | 96.8 | 98.9 | 96.5 | 97.5 | Hot spots & slugging |

The conditions of temperature and contact time (225°±1° C. and a contact time of 22±0.4 seconds) were selected to yield comparative yet favorable results. The HCl conversion was measured and then corrected to adjust for any HCl feed variation from a theoretical 2:1 ratio over ethylene. The reactor design described in the specification was employed. A standard oxychlorination catalyst consisting of cupric chloride on a gamma alumina support was prepared and employed as the Control. The following data was obtained. Catalyst stickiness was also observed and reported.

The data shows that the use of a catalyst of cupric chloride, an alkali metal, and a rare earth metal results in significantly higher % Ethylene efficiency and % HCl conversion than the Control. However, as seen in Experiment 1 catalyst stickiness occurs unless the weight ratio of rare earth metal chloride to alkali metal chloride is at least 0.8 to 1.0 or more. Experiments 3, 4, 9, 10, 11, 13, 14, 16 and 17 show that the use of a level

EXAMPLE I

The following series of experiments were performed to further demonstrate the scope of the catalyst compositions of the present invention. All of the catalysts employed had a cupric chloride level of 10.6% by weight along with the alkali metal salt (potassium chloride) and rare earth metal salt (cerium chloride). The catalysts were prepared and tested in the manner detailed in the Examples above using a molar ratio of reactants of 1.0 ethylene/0.8 oxygen/2.0 HCl at a temperature of 225°±1° C. at a contact time of 22±0.4 seconds. All of the catalysts exhibited good fluidization. The following results were obtained.

TABLE I

| Catalyst | Weight % KCl | Weight % CeCl$_3$ | Weight Ratio of Rare Earth Metal to Alkali Metal | Percent Ethylene Conversion | Percent Ethylene Efficiency | Percent EDC Yield | Percent HCl Conversion Actual | Percent HCl Conversion Corrected |
|---|---|---|---|---|---|---|---|---|
| 1 | 0.5 | 3.0 | 6.0 | 99.6 | 97.8 | 98.2 | 97.3 | 98.1 |
| 2 | 0.7 | 2.0 | 2.9 | 99.6 | 97.6 | 98.0 | 98.6 | 98.0 |
| 3 | 1.0 | 1.0 | 1.0 | 99.6 | 97.8 | 98.2 | 97.3 | 98.3 |
| 4 | 1.0 | 2.0 | 2.0 | 99.9 | 97.6 | 97.7 | 98.4 | 98.4 |
| 5 | 1.5 | 4.0 | 2.7 | 99.2 | 97.5 | 98.3 | 96.3 | 97.8 |
| 6 | 1.5 | 5.0 | 3.3 | 99.5 | 98.2 | 98.7 | 97.0 | 98.6 |
| 7 | 1.0 | 7.0 | 7.0 | 99.8 | 98.1 | 98.4 | 98.3 | 98.6 |
| 8 | 1.0 | 10.0 | 10.0 | 99.0 | 97.7 | 98.7 | 97.5 | 98.0 |
| 9 | 2.0 | 5.0 | 2.5 | 99.1 | 97.4 | 98.3 | 96.4 | 97.8 |
| Control | none | none | — | 99.9 | 93.8 | 93.9 | 94.7 | 95.4 |

EXAMPLE II

Another series of experiments were performed using a catalyst containing 4 percent by weight of various rare earth metal salts in combination with 1.5 percent by weight of potassium chloride. The weight ratio of rare earth metal chloride to alkali metal chloride is 2.7 to 1 in each experiment. Again, the catalysts were prepared and tested following the procedures given in the above Examples. All of the catalysts exhibited good fluidization.

potassium chloride, and 4.0 weight percent cerium chloride. Operating conditions and results are shown below.

TABLE III

| Contact Time (seconds) | Reaction Temperature (°C.) | Percent Ethylene Conversion | Efficiency | Percent EDC Yield | Percent HCl Conversion Actual | Corrected |
|---|---|---|---|---|---|---|
| 16.0 | 219 | 95.4 | 94.8 | 99.4 | 95.5 | 95.2 |
|  | 225 | 98.0 | 96.9 | 98.9 | 97.7 | 97.2 |
|  | 230 | 98.9 | 97.5 | 98.6 | 96.3 | 97.8 |
| 21.6 | 220 | 98.1 | 97.3 | 99.2 | 96.2 | 97.5 |
|  | 224 | 99.2 | 97.5 | 98.3 | 96.3 | 97.8 |
|  | 229 | 99.7 | 97.6 | 98.0 | 96.7 | 98.2 |
| 25.7 | 220 | 99.4 | 97.8 | 98.4 | 96.9 | 98.2 |
|  | 224 | 99.7 | 97.5 | 97.8 | 98.0 | 98.2 |
|  | 230 | 99.9 | 97.3 | 97.4 | 97.4 | 98.2 |
| 32.3 | 220 | 99.8 | 97.7 | 97.9 | 97.5 | 98.2 |
|  | 225 | 99.9 | 97.5 | 97.5 | 97.5 | 98.1 |
|  | 229 | 100.0 | 96.9 | 96.9 | 96.9 | 98.0 |

TABLE II

| Catalyst | Rare Earth Metal | Percent Ethylene Conversion | Efficiency | Percent EDC Yield | Percent HCl Conversion Actual | Corrected |
|---|---|---|---|---|---|---|
| 1 | CeCl$_3$ | 99.2 | 97.5 | 98.3 | 96.3 | 97.8 |
| 2 | LaCl$_3$ | 99.3 | 97.9 | 98.5 | 98.0 | 98.0 |
| 3 | PrCl$_3$ | 99.1 | 98.0 | 98.8 | 98.3 | 98.3 |
| 4 | NdCl$_3$ | 99.3 | 98.2 | 98.8 | 97.2 | 98.4 |
| 5 | $^a$RECl$_3$ | 99.1 | 98.2 | 98.6 | 98.1 | 98.7 |

$^a$mixture of rare earth metals comprised of a majority of cerium and lanthanum, with smaller amounts of neodymium and praeseodymium.

EXAMPLE III

The following data shows that the catalyst compositions of the invention can be used over a wide range of operating conditions. At all conditions, good fluidization was obtained. The catalyst was prepared using the procedure given in Example I. The catalyst contained 10.6 weight percent cupric chloride, 1.5 weight percent Generally, as temperature and contact time increased, percent ethylene conversion and efficiency increased. Percent HCl conversion (except at the lowest operating conditions of 219° C. and 16 seconds contact time) remained fairly constant at a high level.

EXAMPLE IV

The experiments in Example III were essentially repeated using the same catalysts as used in Example III. The following results were obtained.

TABLE IV

| Contact Time (seconds) | Reaction Temperature (°C.) | Percent Ethylene Conversion | Efficiency | Percent EDC Yield | Percent HCl Conversion Actual | Corrected |
|---|---|---|---|---|---|---|
| | | 4% LaCl$_3$ and 1.5% KCl | | | | |
| 21.7 | 219 | 98.8 | 97.7 | 98.9 | 97.3 | 97.9 |
|  | 224 | 99.3 | 97.9 | 98.5 | 98.0 | 98.2 |
|  | 230 | 99.8 | 98.1 | 98.4 | 99.6 | 98.8 |
| 25.7 | 220 | 99.7 | 98.4 | 98.7 | 97.3 | 98.8 |
|  | 224 | 99.8 | 98.3 | 98.5 | 97.5 | 98.8 |
|  | 230 | 99.9 | 97.7 | 97.8 | 97.5 | 98.4 |
| 32.3 | 220 | 99.9 | 98.0 | 98.1 | 97.8 | 98.5 |
|  | 224 | 100.0 | 97.3 | 97.3 | 98.7 | 98.2 |
|  | 229 | 100.0 | 97.1 | 97.1 | 96.3 | 98.2 |
| | | 4% PrCl$_3$ and 1.5% KCl | | | | |
| 21.0 | 220 | 99.3 | 98.2 | 98.8 | 97.1 | 98.7 |
|  | 225 | 99.1 | 98.0 | 98.8 | 98.3 | 98.3 |
|  | 230 | 99.8 | 98.1 | 98.3 | 97.5 | 98.9 |
| 24.8 | 220 | 99.6 | 97.9 | 98.3 | 98.4 | 98.4 |
|  | 225 | 99.8 | 97.4 | 97.6 | 98.8 | 98.2 |
|  | 230 | 99.9 | 98.0 | 98.1 | 97.5 | 99.0 |
| 31.8 | 220 | 100.0 | 97.4 | 97.4 | 97.8 | 98.1 |
|  | 225 | 100.0 | 97.6 | 97.6 | 97.6 | 98.4 |
|  | 230 | 100.0 | 96.3 | 96.3 | 97.2 | 98.1 |
| | | 4% NdCl$_3$ and 1.5% KCl | | | | |
| 21.7 | 220 | 98.6 | 97.7 | 99.1 | 95.9 | 98.0 |
|  | 225 | 99.3 | 98.2 | 98.8 | 97.2 | 98.4 |
|  | 229 | 99.8 | 98.1 | 98.2 | 98.4 | 98.6 |
| 25.7 | 220 | 99.5 | 98.2 | 98.7 | 97.1 | 98.5 |
|  | 225 | 99.8 | 97.9 | 98.1 | 98.0 | 98.4 |
|  | 229 | 100.0 | 97.9 | 97.9 | 97.5 | 98.6 |

TABLE IV-continued

| Contact Time (seconds) | Reaction Temperature (°C.) | Percent Ethylene Conversion | Percent Ethylene Efficiency | Percent EDC Yield | Percent HCl Conversion Actual | Percent HCl Conversion Corrected |
|---|---|---|---|---|---|---|
| 32.3 | 220 | 99.9 | 98.2 | 98.3 | 97.4 | 98.6 |
|  | 225 | 100.0 | 97.5 | 97.5 | 97.5 | 98.0 |
|  | 229 | 100.0 | 96.4 | 96.4 | 97.7 | 97.5 |
| 4% RECl₃ and 1.5% KCl | | | | | | |
| 21.7 | 220 | 99.0 | 97.9 | 98.9 | 97.6 | 98.2 |
|  | 225 | 99.6 | 98.2 | 98.6 | 98.1 | 98.7 |
|  | 230 | 99.8 | 97.6 | 97.9 | 98.4 | 98.3 |
| 25.7 | 220 | 99.6 | 98.1 | 98.5 | 97.9 | 98.5 |
|  | 225 | 99.9 | 98.1 | 98.2 | 98.4 | 98.7 |
|  | 230 | 100.0 | 97.2 | 97.2 | 98.0 | 98.2 |
| 32.3 | 220 | 99.9 | 97.6 | 97.7 | 97.6 | 98.5 |
|  | 225 | 100.0 | 97.4 | 97.4 | 98.1 | 98.3 |
|  | 230 | 100.0 | 96.9 | 96.9 | 98.2 | 98.2 |

We claim:

1. In the process of oxychlorination of ethylene to produce 1,2-dichloroethane by contacting a mixture of ethylene, oxygen and hydrogen chloride with a fluidized catalyst composition in a reaction zone and recovering 1,2-dichloroethane from the effluents of the reaction zone, the improvement which comprises the use of as the catalyst a composition consisting essentially of a fluidizable alumina support having a surface area of from about 80 to about 200 m²/g having deposited thereon from about 4% to about 17% by weight of a copper salt, about 0.25% to about 2.3% by weight of an alkali metal salt(s), and from about 0.2% to about 15% by weight of a rare earth metal salt(s), all weight percents based upon the total weight of the catalyst composition, wherein the weight ratio of the rare earth metal salt(s) to the alkali metal salt(s) in the catalyst composition is at least 0.8:1; and further characterized in that the alkali metal salt(s) and rare earth metal salt(s) are not calcined to the support prior to depositing the copper salt and the reaction is conducted at a temperature of from about 220° C. to about 240° C.

2. The process of claim 1 further characterized in that the ratio of ethylene, HCl, and oxygen employed range from about 1.0 to about 1.1 moles of ethylene and about 0.5 mole to about 0.9 mole of oxygen for every 2.0 moles of HCl.

3. A process of claim 2 wherein the catalyst composition contains from about 8% to about 12% by weight of copper chloride, from about 0.5% to about 2.0% by weight of potassium chloride, and from about 1% to about 10% by weight of cerium chloride.

4. A process of claim 2 wherein the catalyst composition contains from about 8% to about 12% by weight of copper chloride, from about 0.5% to about 2.0% by weight of potassium chloride, and from about 1% to about 10% by weight of a mixture of rare earth metal chlorides of substantially cerium, lanthanum, neodymium, and praeseodymium.

5. An oxychlorination process for the production of 1,2-dichloroethane comprising (a) the reaction of from about 1.0 moles to about 1.1 moles of ethylene and about 0.5 mole to about 0.9 mole of oxygen to every 2.0 moles of HCl in the presence of (b) a catalyst composition consisting essentially of an alumina support having a surface area of from about 80 to about 200 m²/g and having deposited thereon from about 4% to about 17% by weight of a copper salt, from about 0.25% to about 2.3% by weight of an alkali metal salt(s), and from about 0.2% to about 15% by weight of a rare earth metal salt(s), all weights based upon the total weight of the catalyst composition, wherein the weight ratio of the rare earth metal salt(s) to the alkali metal salt(s) is at least 0.8:1, and wherein the alkali metal salt(s) and rare earth metal salt(s) are not calcined to the support prior to depositing the copper salt; and (c) operating at reaction conditions of about 220° C. to about 240° C., at a pressure of from about atmospheric to about 70 psig, and for a contact time of about 10 seconds to about 50 seconds.

6. A process of claim 5 wherein the reaction temperature is from about 220° C. to about 240° C. and the contact time is from about 25 seconds to about 35 seconds, and the catalyst composition contains cupric chloride, potassium chloride, and cerium chloride.

* * * * *